United States Patent [19]

Farooq

[11] Patent Number: 4,853,396
[45] Date of Patent: Aug. 1, 1989

[54] PESTICIDAL COMPOSITIONS

[75] Inventor: Saleem Farooq, Arisdorf, Switzerland

[73] Assignee: Ciba-Geigy Corporation, Hawthorne, N.Y.

[21] Appl. No.: 177,228

[22] Filed: Apr. 4, 1988

[30] Foreign Application Priority Data

Apr. 9, 1987 [CH] Switzerland .......................... 1360/87
Feb. 15, 1988 [CH] Switzerland ............................ 543/88

[51] Int. Cl.⁴ ............................................. A61K 31/425
[52] U.S. Cl. ...................................... 514/333; 546/256
[58] Field of Search ......................... 546/256; 514/333

[56] References Cited

U.S. PATENT DOCUMENTS 3,178,440 4/1965 Siegrist et al. ...................... 546/256
3,458,305 7/1969 Doyle et al. ......................... 546/256

OTHER PUBLICATIONS

Kamiya et al., CA 101:110770n.
Wolf et al., CA 1960, 11289f.
Geldard Lions, CA 62:9122b.

*Primary Examiner*—Jane T. Fan
*Attorney, Agent, or Firm*—Kevin T. Mansfield; Edward McC. Roberts

[57] ABSTRACT

The invention relates to the use of 2,5-bis(pyridyl)-1,3,4-thiadiazoles of formula

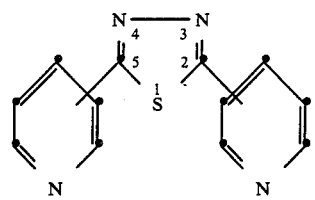

and salts thereof, for controlling pests, especially insects that infest plants and animals. The compounds of formula I are particularly effective against plant-destructive sucking insects.

8 Claims, No Drawings

PESTICIDAL COMPOSITIONS

The invention relates to the use of 2,5-bis(pyridyl)-1,3,4-thiadiazoles for controlling pests and to novel salts and novel compounds having this type of structure.

The invention relates firstly to the use of a compound of formula I

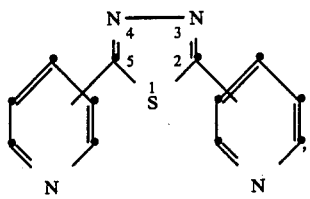

or a salt thereof, for controlling pests.

Preferred compounds of this invention are compounds of formula Ia

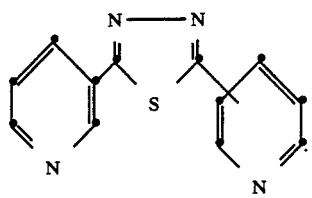

The compound of formula

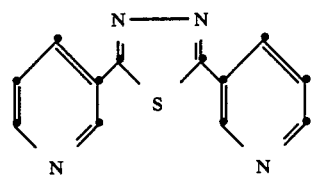

is particularly preferred for the purposes of this invention.

The salts of the compounds of formula I are novel compounds. Accordingly, the invention also relates to the salts, in particular the biocompatible salts, of formula I and to the use thereof as pesticides. Examples of such salts with organic and inorganic acids are: chlorides, bromides, iodides, sulfates, bisulfates, chlorates, perchlorates, rhodanides, nitrates, phosphates, hydrogen phosphates, tetrafluoroborates, formates, acetates, trichloroacetates, trifluoroacetates, phenylsulfonates, oxalates, malonates, succinates, malates, tartrates or citrates.

The invention further relates to the insecticidally highly active per se novel compounds 2, 3 and 4 which are listed in Example 1 of this specification and which fall under formula I.

Pesticidally active 2-(3-pyridyl)-1,3,4-thiadiazoles and 5-(3-pyridyl)-1,2,4-thiadiazoles are disclosed in European patent application No. 0 116 515. Pesticidally active 1,3,4-oxadiazoles of similar structure are disclosed in European patent application No. 0 097 126. Compounds of formula I and compounds of similar structure have already been disclosed in Swiss patent specification Nos. 411 906 and 426 848, wherein the compounds are disclosed as having utility as UV light stabilisers, fluorescent whitening agents or dye intermediates. In contradistinction thereto it has now been found that the compounds of formula I also exhibit excellent activity as pesticides while being well tolerated by plants and having low toxicity to warm-blooded animals. They are especially suitable for controlling pests of plants and animals, in particular insects.

The compounds of formula I which are used and proposed according to this invention can be prepared in a manner known per se q.v. J. Chem. Soc., Perkin Trans., 1 (2), 345–355 (1981); K. N. Zelenin et al., Khim. Geterotsikl. Soedin., No. 7, 904–910 (1982)] by oxidising a compound of formula II

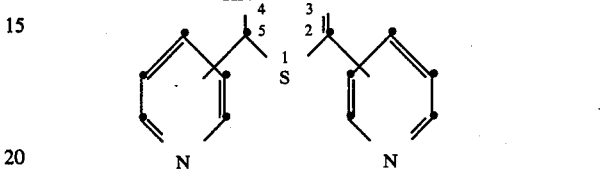

and, in an optional further step, converting the resultant compound of formula I, in conventional manner, into a salt thereof. This process preferably comprises using oxygen as oxidising agent. The process has so far not been used for the preparation of compounds of formula I of this invention.

The compounds of formula I can also be prepared by already known methods by reacting dipyridyl-1,3,4-oxadiazoles of formula III

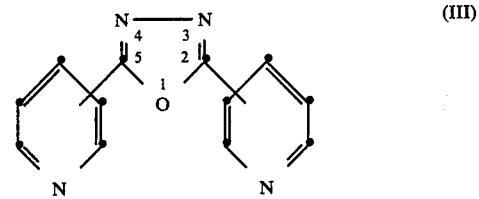

or diacyl hydrazines of formula IV

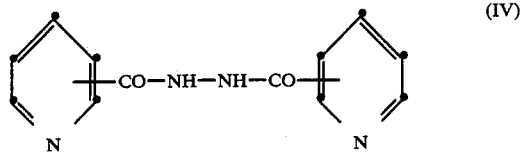

with a phosphorus sulfide, for example $P_2S_5$, preferably in the presence of a tertiary nitrogen base [q.v. Swiss patent specifications Nos. 411 906 and 426 846; J. Am. Chem. Soc. 80, 5201 (1958); J. Het. Chem. 1919 (1981)]. The above starting materials of formulae II, III and IV are known or can be obtained by conventional methods.

In particular, the compounds of formula I are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina.

The good pesticidal activity of the compounds of formula I corresponds to a mortality of at least 50–60% of the above pests.

Most particularly, plant-destructive insects, especially plant-destructive insects in ornamentals and crops of useful plants, in particular in cotton, vegetable, rice and fruit crops, can be controlled with the compounds of formula I. In this connection, particular attention is drawn to the fact that the compounds of formula I have a strongly pronounced systemic as well as contact action against sucking insects, especially against insects of the Aphididae family (e.g. against *Aphis fabae, Aphis craccivora* and *Myzus persicae*) which can only be controlled with difficulty using known pesticides.

The compounds of formula I also exhibit good activity against larval insect stages and nymphs, especially of noxious feeding insects.

The compounds of formula I are also suitable for controlling ectoparasites, e.g. *Lucilia sericata,* and ticks on domestic animals and productive livestock, e.g. by treating animals, barns, stables and pastures.

The activity of the compounds employed and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and *Bacillus thuringiensis* preparations.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical which also includes the alkyl moiety of acyl radicals, e.g. the sodium or calcium salt of lignosulfonic acid, or dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi-(2-chloroethyl)ethylammonium bromide.

The surfactants customarily employed in the art of formulation are described e.g. in "McCutcheon's Detergents and Emulsifiers Annual", MC Publishing Corp., Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower concentration, for example 0.1 to 1000 ppm.

The compositions may also contain further ingredients, such as stabilisers, antifoams, viscosity regulators, binders, tackifiers as well as fertilisers or other active ingredients for obtaining special effects.

EXAMPLE 1

(a)

Preparation of 1-(nicotinoyl)-2-(3-pyridylidene)hydrazine

Five drops of glacial acetic acid are added at room temperature to a solution of 41.1 g of nicotinic acid hydrazide and 32.1 g of pyridine-3-carbaldehyde in 300 ml of ethanol. The reaction mixture, which exotherms slightly, is stirred for ca. 2 hours at room temperature. The precipitated product is isolated by filtration, washed with ca. 100 ml of ethanol and dried, affording the title compound of formula

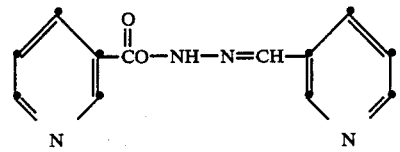

with a melting point of 213°–216° C.

(b)

Preparation of 1-chloro-1,4-di(3-pyridyl)-2,3-diazabutadiene

A suspension of 60.2 g of the 1-(nicotinoyl)-2-(3-pyridylidene)hydrazine obtained according to (a) in 1100 ml of toluene is refluxed and 94.9 g of thionyl chloride are slowly added dropwise to this suspension. After stirring for about 8 hours under reflux, the reaction mixture is concentrated in a rotary evaporator. The residue is dissolved in 700 ml of tetrahydrofuran and the solution is treated with 41 g of triethylamine. After stirring for about 30 minutes at room temperature, the reaction mixture is concentrated in a rotary evaporator and the residue is dissolved in ethyl acetate. The resultant solution is washed once with water and once with a saturated solution of sodium chloride, dried over $Na_2SO_4$ and concentrated by evaporation. The residual crude product is triturated with hot tetrahydrofuran, isolated by filtration and dried, affording the title compound of formula

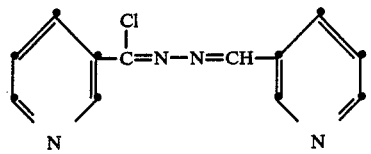

with a melting point of 103°–105° C.

(c)

Preparation of bis-2,5-(3-pyridyl)-4,5-dihydro-1,3,4-thiadiazole

A solution of 6.7 g of 85% potassium hydroxide in 190 ml of ethanol is saturated with hydrogen sulfide. While cooling with ice, 24.3 g of the 1-chloro-1,4-di-(3-pyridyl)-2,3-diazabutadiene obtained in (b) are added in portions to the above solution. The reaction mixture is further stirred for 2 hours at room temperature, concentrated, and the residue is taken up in ethyl acetate. The ethyl acetate solution is then washed once with water and once with a saturated solution of sodium chloride, dried over sodium sulfate, filtered, and concentrated by evaporation. The residue is washed with a mixture of hexane/ether and dried, affording the title compound of formula

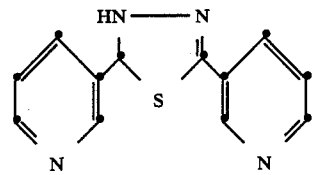

with a melting point of 77°–78° C.

(d)

Preparation of bis-2,5-(3-pyridyl)-1,3,4-thiadiazole

A slow stream of oxygen is passed for ca. 20 hours through a solution, heated to reflux temperature, of 6 g of the bis-2,5-(3-pyridyl)-4,5-dihydro-1,3,4-thiadiazole obtained according to (c) in 70 ml of ethanol. The batch is cooled and the precipitate formed is isolated by filtration and washed with a small amount of ethanol. The crude product is recrystallised from a 1:1:1 mixture of dioxan/ethanol/water and dried under vacuum, affording the title compound of formula

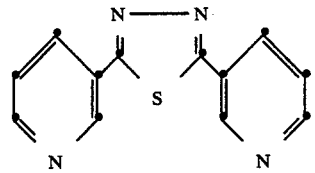

with a melting point of 219°–219.2° C. (compound 1), disclosed in Swiss patent specification No. 411 906.

In conventional and per se known manner (base+acid=salt+water), the oxalate (HOOC—COOH) of m.p. 222°–225° C. and the hydrochloride (2HCl) of m.p. 256°–260° C. are also obtained from compound 1.

The following compounds of formula I are also prepared as described above:

| Compound | | physical data |
|---|---|---|
| 2 | 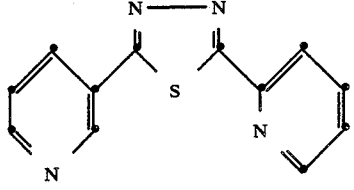 | m.p. 165–166° C. |
| 3 | 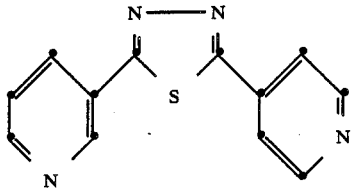 | m.p. 204–205° C. |
| 4 | 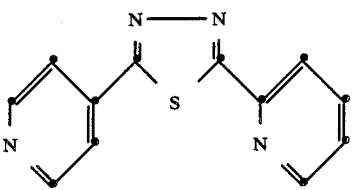 | m.p. 216–217° C. |
| 5 | 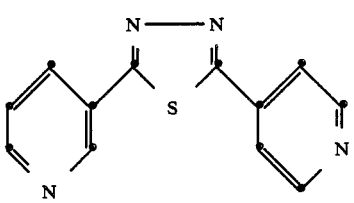 | m.p. 236.5–238° C. (disclosed in Swiss patent 411 906) |
| 6 | 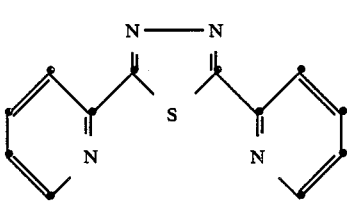 | m.p. 201.3–202.7° C. (disclosed in Swiss patent 411 906) |

EXAMPLE 2

Formulations for compounds of formula I or combinations thereof with other insecticides or acaricides (throughout, percentages are by weight)

| 1. Wettable powders | (a) | (b) | (c) |
|---|---|---|---|
| compound of formula I or combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient or combination is thoroughly mixed with the adjuvants and the mixture is thoroughly ground in a suitable mill, affording wettable powders which can be diluted with water to give suspensions of the desired concentration.

| 2. Emulsifiable concentrate | |
|---|---|
| compound of formula I or combination | 10% |
| octylphenol polyethylene glycol ether (4–5 mol of ethylene oxide) | 3% |
| calcium dodecylbenzenesulfonate | 3% |
| castor oil polyglycol ether (36 mol of ethylene oxide) | 4% |
| cyclohexanone | 30% |
| xylene mixture | 50% |

Emulsions of any required concentration can be obtained from this concentrate by dilution with water.

| 3. Dusts | (a) | (b) |
|---|---|---|
| compound of formula I or combination | 5% | 8% |
| talcum | 95% | — |
| kaolin | — | 92% |

Ready for use dusts are obtained by mixing the active ingredient with the carrier, and grinding the mixture in a suitable mill.

| 4. Extruder granulate | |
|---|---|
| compound of formula I or combination | 10% |
| sodium lignosulfonate | 2% |
| carboxymethylcellulose | 1% |
| kaolin | 87% |

The active ingredient or combination is mixed and ground with the adjuvants, and the mixture is subsequently moistened with water. The mixture is extruded and then dried in a stream of air.

| 5. Coated granulate | |
|---|---|
| compound of formula I or combination | 3% |
| polyethylene glycol (mol. wt. 200) | 3% |
| kaolin | 94% |

The finely ground active ingredient or combination is uniformly applied, in a mixer, to the kaolin moistened with polyethylene glycol. Non-dusty coated granulates are obtained in this manner.

| 6. Suspension concentrate | |
|---|---|
| compound of formula I or combination | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or combination is intimately mixed with the adjuvants, giving a suspension concentrate from which suspensions of any desired concentration can be obtained by dilution with water.

BIOLOGICAL EXAMPLES

EXAMPLE 3

Action against *Musca domestica*

50 g of freshly prepared CMSA nutrient substrate for maggots are charged into each of a number of beakers. A specific amount of an acetonic solution containing 1% by weight of the respective test compound is pipetted onto the nutrient substrate present in the beakers to give an active ingredient concentration of 400 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with the test compound at the given concentration. After the maggots have pupated, the pupae are separated from the substrate by flushing them out with water and then deposited in containers closed with a perforated top. Each batch of flushed out pupae is counted to determine the toxic effect of the test compound on the maggot development. A count is then made after 10 days of the number of flies which have hatched out of the pupae.

Compounds of formula I show good activity in this test.

EXAMPLE 4

Action against *Aëdes aegypti*

A concentration of 400 ppm is obtained by pipetting a specific amount of a 0.1% solution of the test compound in acetone onto the surface of 150 ml of water in a beaker. After the acetone has evaporated, 30 to 40 two-day-old larvae of *Aëdes aegypti* are put into the beaker containing the test compound. Mortality counts are made after 2 to 7 days.

Compounds of formula I show good activity in this test.

EXAMPLE 5

Insecticidal contact action against *Aphis craccivora*

Before the start of the test, 4- to 5-day old pea seedlings reared in pots (20 ml) are each populated with about 200 insects of the species *Aphis craccivora*. The treated plants are sprayed direct to drip point 24 hours later with an aqueous formulation containing the test compound in a concentration of 400 ppm. Two plants are used for each test compound at its given concentration. A mortality count is made after 3 and 5 days respectively. The test is carried out at 21°-22° C. and at a relative humidity of about 55%.

The compounds of formula I show good activity in this test.

EXAMPLE 6

Insecticidal systemic action against *Aphis craccivora* (soil)

4- to 5-day-old pea seedlings (about 2 cm high) in pots (12 cm diameter) containing 600 ccm of soil are infested with *Aphis craccivora* (about 200 aphids per pot). Each pot contains 4 seedlings on which the aphid populations develop. After 24 hours, 50 ml of an aqueous emulsion formulation of the test compounds (prepared from a 25% wettable powder) in a concentration of 400 ppm are poured direct on to the soil in the pots.

Evaluation of the mortality of the test insects is made 2 and 3 days after application. Four plants in a separate pot, are used for each test compound. The test is carried out at 25° C. and ca. 70% relative humidity.

The compounds of formula I show good activity in this test.

EXAMPLE 7

Contact action against *Myzus persicae*

4- to 5-day old pea plants which have been reared in water are each populated with about 200 aphids of the species *Myzus persicae* before the start of the test. The treated plants are sprayed direct to drip point 24 hours later with an aqueous suspension containing the test compound in a concentration of 12.5 ppm. Two plants are used for each compound at its given concentration. An evaluation of percentage mortality is made 24, 48 and 72 hours respectively, after application. The test is carried out at 21°-22° C. and about 60% relative humidity.

Compound 1 according to Example 1 effects 80 to 100% kill in this test.

EXAMPLE 8

Systemic action against *Myzus persicae* (soil)

Pimenta plants which have grown roots are transplanted in the 4- to 5-leaf stage into pots containing 60 ccm of soil. The plants are then populated with 200 aphids of the species *Myzus persicae*. Then 50 ml of an aqueous formulation (prepared from a 25% wettable powder) of the test compound in a concentration of 400 ppm are poured direct onto the soil present in the pots.

The evaluation of percentage mortality is made 3 and 7 days after the start of the test. Two plants, each in a separate pot, are used for each test substance at its given concentration. The test is carried out at about 25° C. and 60% relative humidity.

Compounds of formula I exhibit good activity in this test.

EXAMPLE 9

Systemic action against *Myzus persicae* (in water)

Pea seedlings (ca. 2 cm in height) which have been populated 24 hours before the start of the test with ca. 200 aphids of the species *Myzus persicae* are put into 20 ml of an aqueous spray mixture containing 100 ppm of the test compound. The spray mixture is prepared from an emulsifiable concentrate or a wettable powder and is present in a vessel (volume: 150 ml) which is sealed with a perforated plastic cover. The root of the pea plantlet is pushed through the centre hole in the plastic cover into the aqueous formulation. This hole is then plugged with cotton wool to fix the plant. The test is carried out at 21° C. and 60% relative humidity. After 2, 3 and 6 days a percentage evaluation is made of aphids which are no longer capable of sucking in order to establish whether the test compound absorbed through the roots is able to kill the insects present on the upper parts of the plants.

Compound 1 according to Example 1 effects 80-100% systemic action against insects of the species *Myzus persicae* in this test.

EXAMPLE 10

Leaf penetration action against *Aphis craccivora*

A small shoot of *Vicia faba*, which is heavily infested with aphids of the species *Aphis craccivora*, is placed in each of a number of 8 cm high plastic beakers (diameter about 6 cm). Each beaker is covered with a cardboard lid having a punched opening of 2 cm diameter in the centre. A leaf of a *Vicia faba*-plant is then placed over the opening in the lid without separating this leaf from the potted plant. The leaf is then fixed on the beaker with a second punched cardboard lid above the opening of the first lid. From underneath, i.e. through the opening of the first lid, the aphids in the beaker then infect the leaf of the plant used as bait. An aqueous formulation of the test compound is then applied in a concentration of 100 ppm uniformly with a brush to the top side of the leaf. An investigation is then made to determine whether the test substance applied to the top side of the leaf of the plant used as bait has diffused in sufficient amount through the leaf to its underside to kill aphids sucking thereon.

The test is carried out at about 21° C. and 60% relative humidity. The evaluation of percentage mortality is made 24 and 48 hours after application of the test compound.

Compound 1 according to Example 1 effects 80-100% in this test.

What is claimed is:

1. A method of controlling pests selected from insects and representatives of the order Acarina, which comprises treating said pests, their different development stages and/or the locus thereof, with a pesticidally effective amount of a compound of formula I

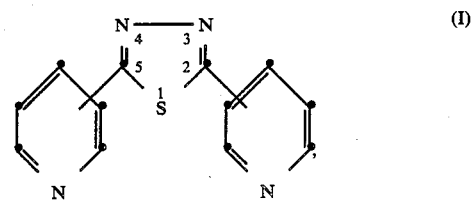

or a salt thereof, or with a composition containing such a compound or salt thereof, together with adjuvants and carriers.

2. The method of claim 1, which comprises the use of a compound of formula Ia

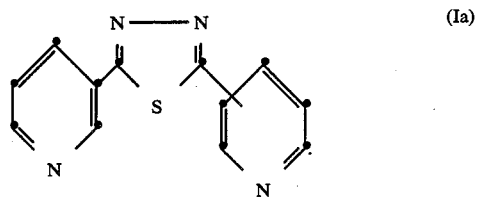

3. The method of claim 1, which comprises the use of a compound of formula

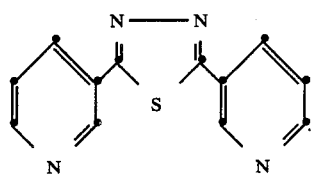

4. The method of claim 1, which comprises the use of a compound of formula

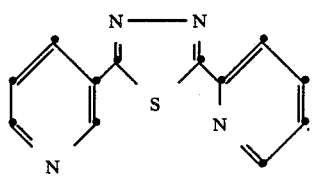

5. The method of claim 1, which comprises the use of a compound of formula

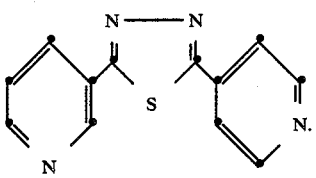

6. The method of claim 1, which comprises controlling insects and representatives of the order Acarina on animals and plants.

7. The method of claim 6, wherein the insects to be controlled are plant-destructive insects.

8. The method of claim 7, wherein the insects to be controlled are plant-destructive sucking insects.

* * * * *